United States Patent [19]
Ogawa et al.

[11] Patent Number: 6,123,927
[45] Date of Patent: *Sep. 26, 2000

[54] COSMETIC COMPOSITION CONTAINING SPINDLE SHAPED FINE PARTICLES OF TITANIUM DIOXIDE

[75] Inventors: Katsuki Ogawa; Sadaki Takata; Shigenori Kumagaya, all of Yokohama, Japan

[73] Assignee: Shiseido Company, Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/860,918

[22] PCT Filed: Nov. 22, 1996

[86] PCT No.: PCT/JP96/03442

§ 371 Date: Jul. 14, 1997

§ 102(e) Date: Jul. 14, 1997

[87] PCT Pub. No.: WO97/18793

PCT Pub. Date: May 29, 1997

[30] Foreign Application Priority Data

Nov. 22, 1995 [JP] Japan .................................. 7-328431

[51] Int. Cl.$^7$ ....................................................... A61K 7/42
[52] U.S. Cl. .............................. 424/59; 514/937; 514/938
[58] Field of Search ............................... 424/59; 514/937, 514/938

[56] References Cited

U.S. PATENT DOCUMENTS

| | | |
|---|---|---|
| 4,810,490 | 3/1989 | Dixon ........................................ 424/59 |
| 4,927,464 | 5/1990 | Cowie . |
| 5,443,759 | 8/1995 | Dahms . |
| 5,516,457 | 5/1996 | Dahms . |
| 5,543,135 | 8/1996 | Dahms . |

FOREIGN PATENT DOCUMENTS

| | | |
|---|---|---|
| 2212414 | 8/1990 | Japan . |
| 55262634 | 10/1993 | Japan . |
| 07165532 | 6/1995 | Japan . |
| 07258055 | 10/1995 | Japan . |

*Primary Examiner*—Rebecca Cook
*Attorney, Agent, or Firm*—Norris, McLaughlin & Marcus, P.A.

[57] ABSTRACT

This invention relates to a cosmetic composition having a UV blocking action in a wide region from UVB to UVA and capable of preventing erythema and melanism due to burning by the sun.

The conventional fine particles of titanium dioxide are insufficient in the effect for blocking ultraviolet ray and, furthermore, the feeling to the skin becomes poorer, and the finish becomes powdery.

This invention resides in the formulation, into a cosmetic composition, of spindle shaped fine particles of titanium dioxide having an average short diameter of 0.03 to 0.06 $\mu$m, an average long diameter of 0.08 to 0.12 $\mu$m, and an aspect ratio (long diameter/short diameter) of 2 to 4 or the spindle shaped fine particles and a metal oxide having an average particle size of 0.2 $\mu$m or more.

11 Claims, 11 Drawing Sheets

COSMETIC COMPOSITION CONTAINING SPINDLE SHAPED FINE PARTICLES OF TITANIUM DIOXIDE

This is a 371 of PCT/JP96/03442 filed Nov. 21, 1996.

TECHNICAL FIELD

The present invention relates to a cosmetic composition having a UV blocking action in a wide region from UVB to UVA and capable of preventing erythema and melanism due to burning by the sun.

BACKGROUND ART

In the past, sun screens, foundations, etc. have been known as cosmetic compositions for preventing sunburn. In these cosmetic compositions UV absorbents and UV blocking agents are formulated as substances for blocking UV rays. In these, fine particles of titanium dioxide having an average particle size of 0.03 to 0.05 µm have been generally used as UV blocking agents. The applicant of the present invention previously obtained a cosmetic composition having a high UV protective effect by formulating a combination of spherical fine particles of titanium dioxide having an average particle size of 0.01 to 0.10 µm and needle type (spindle shaped) fine particles of titanium dioxide having a short diameter of 0.005 to 0.02 µm and a long diameter of 0.01 to 0.10 µm (Japanese Patent Application No. 5-340571 (i.e., JP-A-7-165532)).

However, these fine particles of titanium dioxide are hard to disperse in the single particle state in a cosmetic composition since the particle size is small. Therefore, in actuality, they exist as considerably large aggregates. Further, when metal oxides having a large relative particle size are formulated in a cosmetic composition, the metal oxides form the nucleus for easy formation of aggregates and the effect for preventing UV rays inherently exhibited remarkably falls. In particular, in a solid foundation, since the components are a powder and oil in a paste composition, the fine particles of powder easily aggregate as nuclei the relatively large particle size powder. The above trend becomes particularly conspicuous. Accordingly, even if fine particles of titanium dioxide are formulated in the cosmetic composition, it is hard to obtain the desired UV protecting effect. Even if the amount of formulation is increased, the effect for protecting the UV rays will not rise, the feeling to the skin will become poorer, the finish will become powdery, and other defects will appear.

Further, fine particles of titanium dioxide have the effect for blocking UVB of the region of 290 nm to 320 nm, but are insufficient in the effect for blocking UVA having a region of 320 nm to 400 nm, and therefore, have had the defect of not being able to prevent skin disorders due to UVA—which have recently been taken up as an issue.

DISCLOSURE OF INVENTION

The present inventors newly designed the fine particles of titanium dioxide so as to overcome the above-mentioned defects in fine particles of titanium dioxide. That is, the present inventors conducted theoretical calculations based on the Mie theory (P. Stamatakis et al., J. Coatings Teck., 62 (10), 95 (1990) on the dependency of the titanium dioxide optical scattering and UV protection effect on the particle size. As a result, it was found that, at a wavelength of 300 nm, a particle size having 0.03 to 0.06 µm gave the highest blocking effect, at 350 nm, a particle size of 0.08 µm was optimal, and at 400 nm, a particle size of 0.12 µm was optimal. Further, as a result of the verification of the effect of the particle shape which was supposed to reduce the aggregation of powder in the cosmetic composition, it was discovered that the dispersion of the particles having the spindle shape rather than a spherical shape was high and the UV blocking effect was high. Therefore, the present inventors designed spindle shaped fine particles of titanium dioxide having a long diameter of an optimal particle size for blocking the UVA, that is, approximately 0.10 µm, and a short diameter of an optimal particle size for blocking the UVB, that is, of 0.03 to 0.06 µm. Further, the present inventors found that fine particles of titanium dioxide synthesized faithfully to the particle design are not that susceptible to the effects of the metal oxides having a relatively large particle size in the cosmetic composition and are superior in dispersion. They found that this had the high effect for blocking a wide range of UV rays from UVB to UVA.

That is, in accordance with the present invention, there is provided a cosmetic composition comprising spindle shaped fine particles of titanium dioxide of an average short diameter having 0.03 to 0.06 µm, an average long diameter of 0.08 to 0.12 µm, and an aspect ratio (i.e., long diameter/short diameter) of 2 to 4, formulated therein.

In accordance with the present invention, there is also provided a cosmetic composition according to claim 1, wherein said average short diameter is 0.03 to 0.04 µm, the average long diameter is 0.09 to 0.10 µm, and the aspect ratio is 2.5 to 3.5.

BRIEF DESCRIPTION OF DRAWINGS

The present invention will now be explained in detail with reference to the drawings; wherein.

BEST MODE FOR CARRYING OUT THE INVENTION

Figure 1:
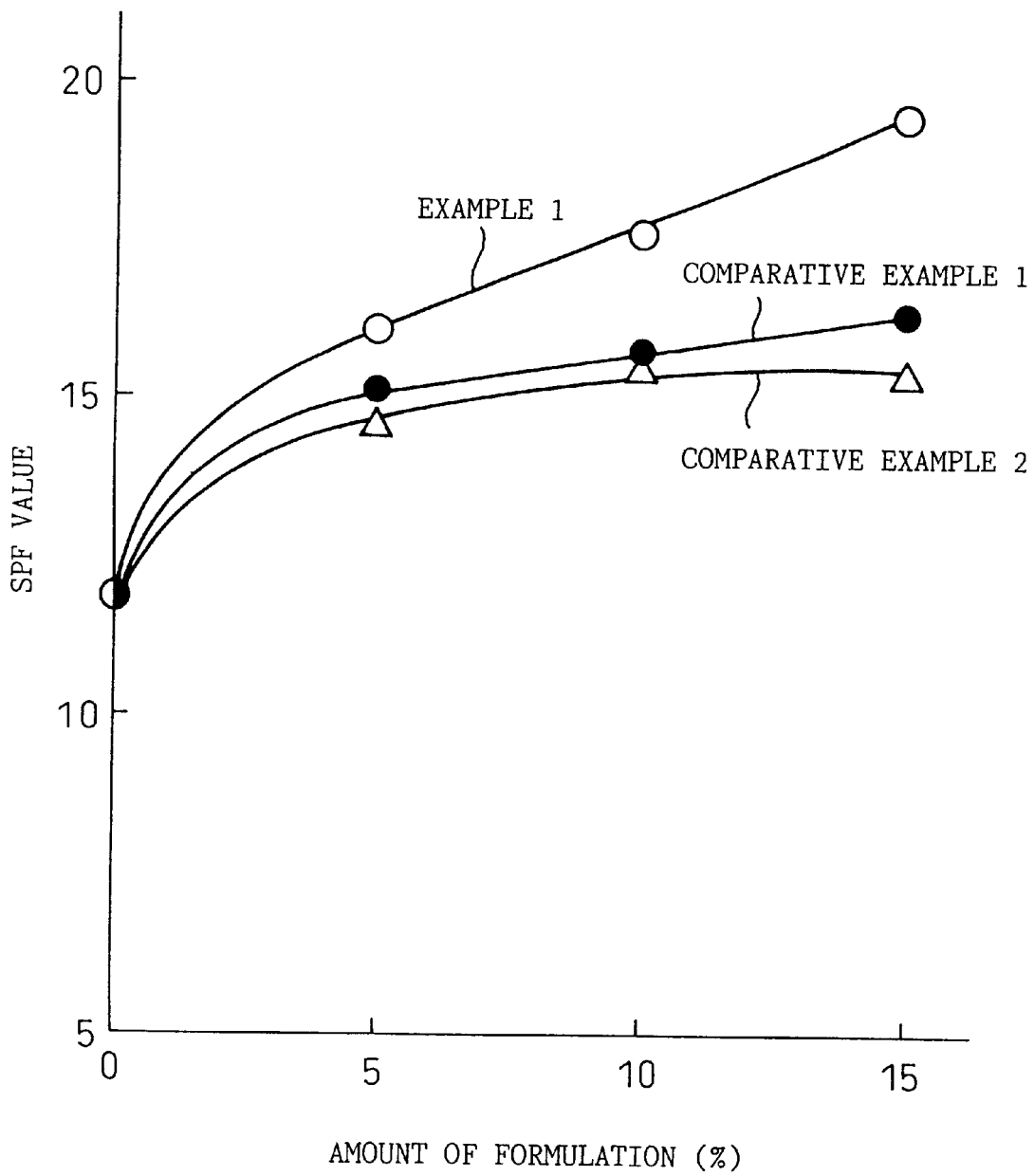
FIG. 1 is a graph showing the relationship between the amount of formulation and an SPF value of the spindle shaped fine particles of titanium dioxide of the present invention, compared with the prior art.

The configuration of the present invention will be explained in detail below.

The spindle shaped fine particles of titanium dioxide used in the present invention have a rutile type crystalline structure, an average short diameter of the primary particles having 0.03 to 0.06 μm, preferably 0.03 to 0.04 μm, and an average long diameter of the primary particles having 0.08 to 0.12 μm, preferably 0.09 to 0.10 μm. If the average short diameter and the average long diameter are smaller than these values, the UV blocking effect at the different wavelengths becomes weaker due to the above reasons, while if larger, the transparency in the visible light region is remarkably detracted from and disadvantageous effects are seen such as the finish of the sun screen or foundation becoming white. Further, the aspect ratio (long diameter/short diameter) is 2 to 4, preferably 2.5 to 3.5. If the aspect ratio is smaller than 2 or is larger than 4, the blocking power of either of the UVB or UVA becomes inferior and it becomes difficult to block both the UVB and UVA well. This is considered to be because, as a result of the particle design of the titanium dioxide relating to the protection from ultraviolet light, the optimal particle size for absorption or scattering at the different wavelengths based on the Mie theory etc. is 0.03 to 0.04 μm at 300 nm and near 0.12 μm at 400 nm, so when converted to an aspect ratio, the spindle shaped particles of titanium dioxide having an aspect ratio of about 3 has an ability to block UVB and UVA is superior at a broad region of 300 to 400 nm.

Further, it is possible to apply any sort of surface treatment performed in the past on the spindle shaped fine particles of titanium dioxide. Depending upon the formulation form, it is preferable to apply the surface treatment thereto with silicone, aluminum stearate, aluminum oxide, dextrin aliphatic acid acid, lauroyl lysine, fluorine, cerium oxide, zirconium oxide, tungsten oxide, aluminum hydroxide, polyols, amines, alkanolamines, polymer silicon compounds, polyacrylamides, polyacrylic acids, carboxymethylcellulose, xanthane gum, surfactants, etc. so as to ensure greater dispersion and stable presence in the cosmetic composition.

The spindle shaped fine particles of titanium dioxide according to the present invention may be used in the cosmetic composition in the range of 0.5 to 70.0% by weight, preferably 2.0 to 40.0% by weight.

As the process for production of the spindle shaped fine particles of titanium dioxide according to the present invention, the conventionally known sulfuric acid method may be used. That is, crude ore ilmenite is dissolved in sulfuric acid, then the iron is removed as $FeSO_4$. The separated titanyl sulfate is hydrolyzed, the hydrous titanium dioxide thus obtained is washed, then this is preliminarily sintered at 400 to 900° C. and pulverized to obtain the spindle shaped fine particles of titanium dioxide as a powder. In this sintering process, the moisture of the hydrous titanium dioxide is slowly evaporated at a high temperature to promote the growth of the particles. The particles which are formed hold a certain fixed size and exhibit a substantially equivalent spindle shape.

The spindle shaped fine particles of titanium dioxide according to the present invention, as explained above, do not aggregate even when making dual use of relatively large particle size metal oxides and can hold the desired UV protective effect. Accordingly, the cosmetic of the present invention is particularly effective in the case of a cosmetic formulated using a powder of a pigment, particular, a metal oxide, as an essential ingredient, for example, a solid type foundation or emulsified foundation.

Therefore, according to the present invention, there is provided a cosmetic composition comprising spindle shaped fine particles of titanium dioxide having an average short diameter of 0.03 to 0.06 μm, an average long diameter of 0.08 to 0.12 μm, and an aspect ratio (long diameter/short diameter) of 2 to 4 and metal oxides of a primary particle average particle size having at least 0.2 μm.

Here, as the metal oxide of an average particle size having at least 0.2 μm, preferably 0.3 to 1.0 μm, hydrates of metal oxides such as titanium dioxide, niobium oxide, silicon dioxide, aluminum oxide, zinc oxide, hafnium oxide, thorium oxide, stannous oxide, thallium oxide, zirconium oxide, beryllium oxide, cobalt oxide, calcium oxide, magnesium oxide, molybdenum oxide, and other metal oxides, hydrous titanium dioxide, hydrous niobium oxide, hydrous silicon dioxide, hydrous aluminum oxide, hydrous zinc oxide, hydrous halfnium oxide, hydrous thorium oxide, hydrous stannous oxide, hydrous thallium oxide, hydrous zirconium oxide, hydrous beryllium oxide, hydrous cobalt oxide, hydrous calcium oxide, hydrous magnesium oxide, and hydrous molybdenum oxide may be used.

Among the metal oxides having average particle sizes of at least 0.2 μm, the ones particularly preferred are titanium dioxide, zinc oxide, iron oxide, and cerium oxide and their hydrates.

The amount of formulation of the metal oxides having average particle sizes of at least 0.2 μm is preferably 1.0 to 40.0% by weight in all cosmetics compositions.

The cosmetic composition of the present invention may contain a powder other than the above. As such a powder, inorganic powders such as talc, kaolin, mica, sericite, dolomite, phlogopite, synthetic mica, lepidolite, biotite, lithia mica, vermiculite, magnesium carbonate, calcium carbonate, diatomaceous earth, magnesium silicate, calcium silicate, aluminum silicate, barium silicate, barium sulfate, stronthium silicate, tungstenate metal salts, silica, magnesium oxide, calcium oxide, zeolite, boronitride, and ceramic powder; organic powders such as nylon powder, polyethylene powder, benzoguanamine powder, ethylene tetrafluoride powder, microcrystalline cellulose; inorganic white pigments such as titanium dioxide, zinc oxide; inorganic red pigments such as iron oxide (bengara), iron titanate; inorganic brown pigments such as γ-iron oxide, inorganic yellow pigments such as yellow iron oxide, yellow ocher; inorganic black pigments such as black iron oxide, carbon black; inorganic violet pigments such as mango violet, cobalt violet; inorganic green pigments such as chromium oxide, chromium hydroxide, cobalt titanate; inorganic blue pigments such as Prussian blue, navy blue; pearl pigments such as, titanium dioxide covered mica, titanium dioxide covered bismuth oxichloride, bismuth oxichloride, titanium dioxide covered talc, fish scale flake, colored titanium dioxide covered mica; and other metal powder pigments such as aluminum powder, copper powder; organic pigments such as Red No. 201, Red No. 202, Red No. 204, Red No. 205, Red No. 220, Red No. 226, Red No 228, Red No. 405, Orange No. 203, Orange No. 204, Yellow No. 205, Yellow No. 401, Blue No. 404, and organic pigments such as, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, zirconium, barium, or aluminum lakes, etc.

The cosmetic compositions of the present invention can be more effective sunburn protecting cosmetic compositions by further formulating thereinto the conventionally known needle shaped fine particles of titanium dioxide having an average short diameter of 0.005 to 0.02 $\mu$m and an average long diameter of 0.01 to 0.1 $\mu$m so as to block out UV rays in a broad region from UVB to UVA. In this case, the amount of the needle shaped fine particles of titanium dioxide used is 0.5 to 50.0% by weight, preferably 1.0 to 30.0% by weight.

The form of the cosmetic composition of the present invention is not particularly limited, but a solid foundation, powder, oily stick, W/O (water-in-oil) or O/W (oil-in-water) emulsion, etc. are general. In particular, a solid foundation or oily stick foundation is a mixture of a power, oil, and wax, and therefore the conventional fine particles of titanium dioxide agglomerate and the anticipated effect is hard to achieve, whereas the formulation of the spindle shaped fine particles of titanium dioxide according to the present invention is extremely effective.

Further, in the case of a W/O (water-in-oil) type suspension, as a means for raising the water resistance (waterproofing effect), a coating agent of silicone resin etc. may be used, but the conventional fine particles of titanium dioxide agglomerate and the anticipated effects are hard to obtain. Thus, the formulation of the spindle shaped fine particles of titanium dioxide according to the present invention is extremely effective. In this case, the amount of the silicone resin formulated therein is at least 0.5% by weight of the total weight of the composition, preferably 1.0% by weight to less than 10% by weight. As the silicone resin, a copolymer comprised of one or more types of structural units of $SiO_2$, $RSiO_{3/2}$, $R_2SiO$ (wherein R is hydrogen, a $C_1$ to $C_6$ hydrocarbon group, or a phenyl group) or a copolymer with an end sealed by $RSiO_{3/2}$ (wherein R is the same as defined above) may be exemplified.

As the other components of the cosmetic composition of the present invention, general components of cosmetic compositions may be used in so far as the spindle shaped fine particles of titanium dioxide can be included in the cosmetic composition to an extent where exhibiting their object. As such components, a higher alcohol, lanolin derivative, protein derivative, polyethylene, glycol aliphatic acid ester oil, silicone oil, paraffinic oil, fluorine oil, or other oil component, propylene glycol, glycerine, polyethylene glycol, or other moisture retaining agent, oil soluble polymer substance, water-soluble polymer substance, ion exchange water, alcohol, preservative, bactericide, pH adjuster, antioxidant, dye, fragrance, and other additives may be exemplified. These may be called cosmetic basic components in the present invention.

EXAMPLES

The present invention will now be explained in detail with reference to the following Examples. The present invention, however, is not limited to these Examples. The amounts of formulation are % by weight.

Example 1 and Comparative Examples 1 to 2

The solid foundations comprising the composition (parts by weight) listed in the following Table 1 were prepared by the method explained later.

The UV preventing effect was measured by the measurement method developed by the present applicant (see Japanese Patent Application No. 5-239875) giving an SPF value (in vitro) extremely close to the SPF value (in vivo) by measurement prescribed by the U.S. FDA and was evaluated by the same. Further, the UVA was evaluated by a measurement method (in vitro) with a high correlation to the PFA value (in vivo) obtained by the PFA (Protection Factor of UVA) measurement giving an indicator of the protection against melanism of the skin caused by the UVA as defined by a special committee on UV rays of the Japan Cosmetic Industry Federation. The results are shown in FIG. 1 and FIG. 2.

Figure 2:
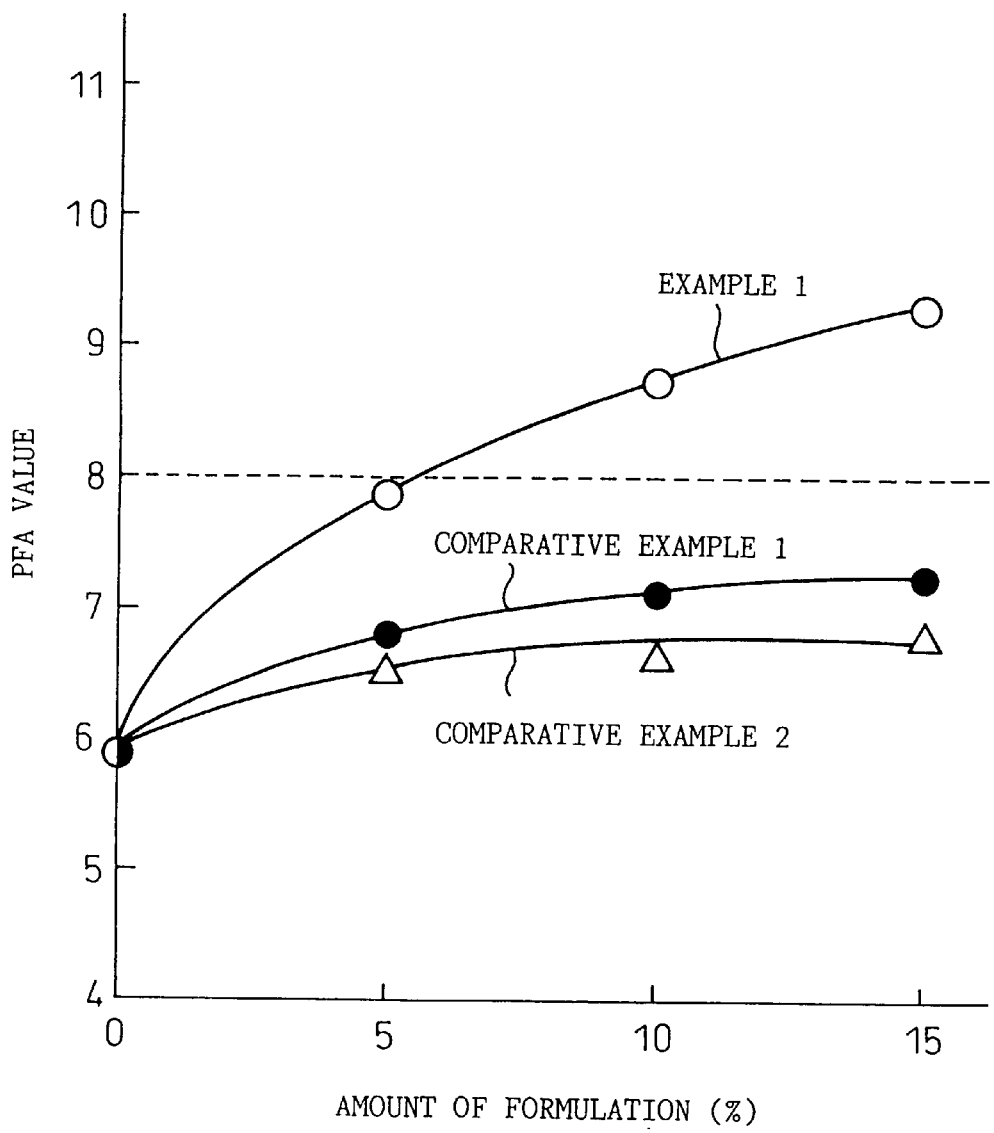
FIG. 2 is a graph showing the relationship between the amount of formulation and a PFA value of the spindle shaped fine particles of titanium dioxide of the present invention compared with the prior art.

As will be understood from FIG. 1 and FIG. 2, the cosmetic composition of the present invention, compared with Comparative Examples 1 and 2 containing, as a pigment, 0.2 $\mu$m or more of a metal oxide such as of titanium dioxide and using fine particles of titanium dioxide of a small particle size used as a UV blocking agent in the past, exhibits a high UV protective effect with respect to both of the UVA and UVB. This effect is particularly remarkable in the UVA region.

(Method of Production)

The powder components of (1) to (11) were homogeneously mixed by a Henschel mixer, then the oil components of (12) to (16) were dropwise added and mixed by the Henschel mixer. The resultant mixture was pulverized by a pulverizer, then was placed on a metal or plastic plate and compression molded to form the solid foundation.

TABLE 1

| | Example | Comparative Example | |
|---|---|---|---|
| | 1 | 1 | 2 |
| (1) Silicone-treated mica | 35–45 | 35–45 | 35–45 |
| (2) Silicone-treated mica | 15.0 | 15.0 | 15.0 |
| (3) Silicone-treated spherical resin powder | 10.0 | 10.0 | 10.0 |
| (4) Silicone-treated bengara (0.2–0.5 $\mu$m) | 0.6 | 0.6 | 0.6 |
| (5) Silicone-treated yellow iron oxide (0.3–0.7 $\mu$m) | 1.0 | 1.0 | 1.0 |
| (6) Silicone-treated black iron oxide (0.2–0.5 $\mu$m) | 0.1 | 0.1 | 0.1 |
| (7) Silicone-treated titanium dioxide (0.2–0.6 $\mu$m) | 10.0 | 10.0 | 10.0 |
| (8) Silicone-treated spherical fine particles of titanium dioxide (A)*[1] | — | 5–15 | — |
| (9) Silicone-treated needle-shaped fine particles of titanium dioxide (B)*[2] | — | — | 5–15 |
| (10) Silicone-treated spindle shaped fine particles of titanium dioxide (C)*[3] | 5-15 | — | — |
| (11) Paraben | q.s. | q.s. | q.s. |
| (12) Dimethyl polysiloxane | 3.0 | 3.0 | 3.0 |
| (13) Liquid paraffin | 4.0 | 4.0 | 4.0 |
| (14) Methylphenyl polysiloxane | 3.0 | 3.0 | 3.0 |

TABLE 1-continued

|  | Example | Comparative Example | |
|---|---|---|---|
|  | 1 | 1 | 2 |
| (15) Vaseline | 3.0 | 3.0 | 3.0 |
| (16) Antioxidant | q.s. | q.s. | q.s. |

Figure 10:
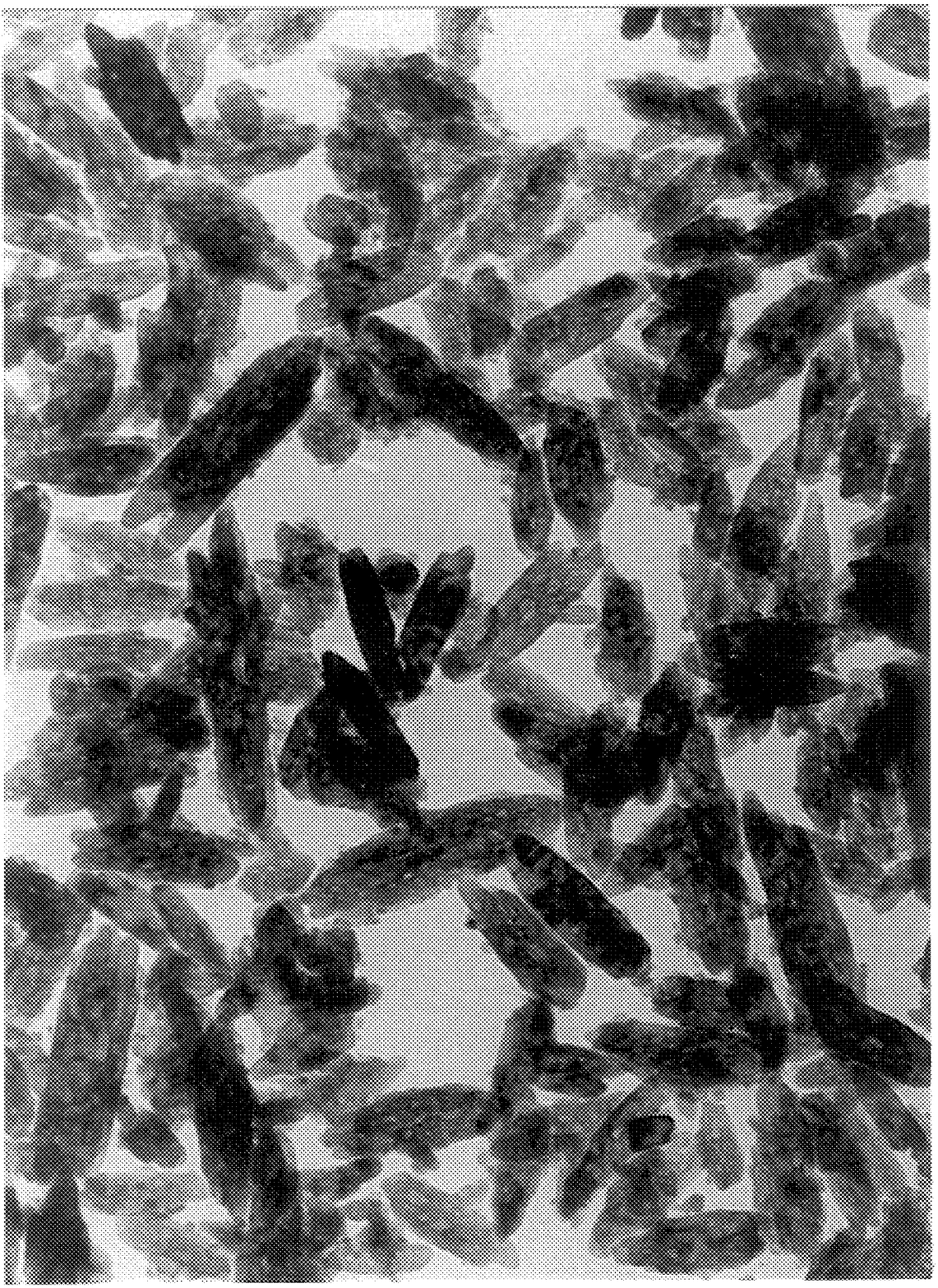
FIG. 10 is an electron micrograph (X150,000) in place of a drawing showing the particle structure of the spindle shaped fine particles of titanium dioxide of the present invention.
Figure 11:
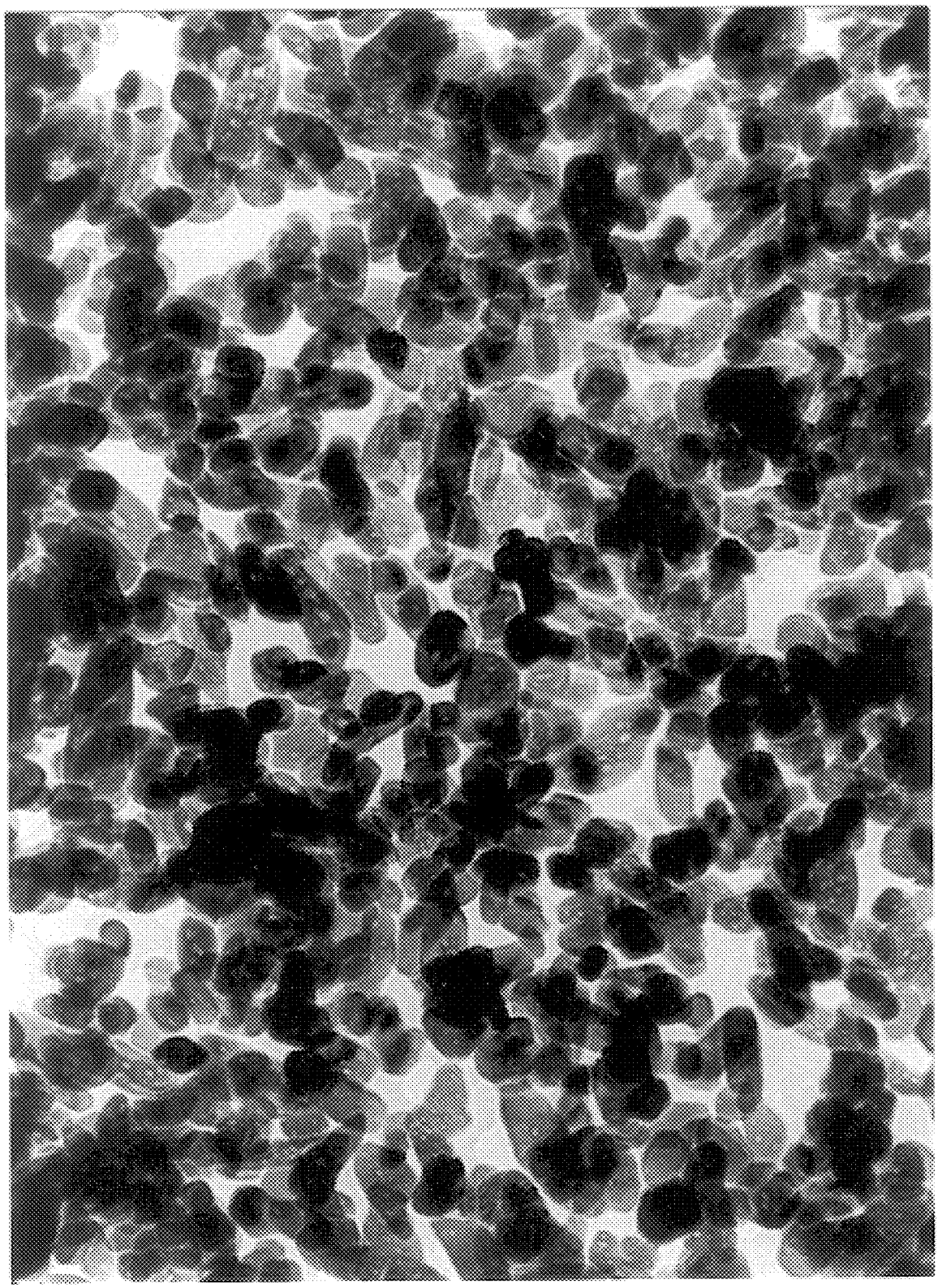
FIG. 11 is an electron micrograph (X150,000) in place of a drawing showing the particle structure of the spherical fine particles of titanium dioxide of the prior art.
Figure 12:
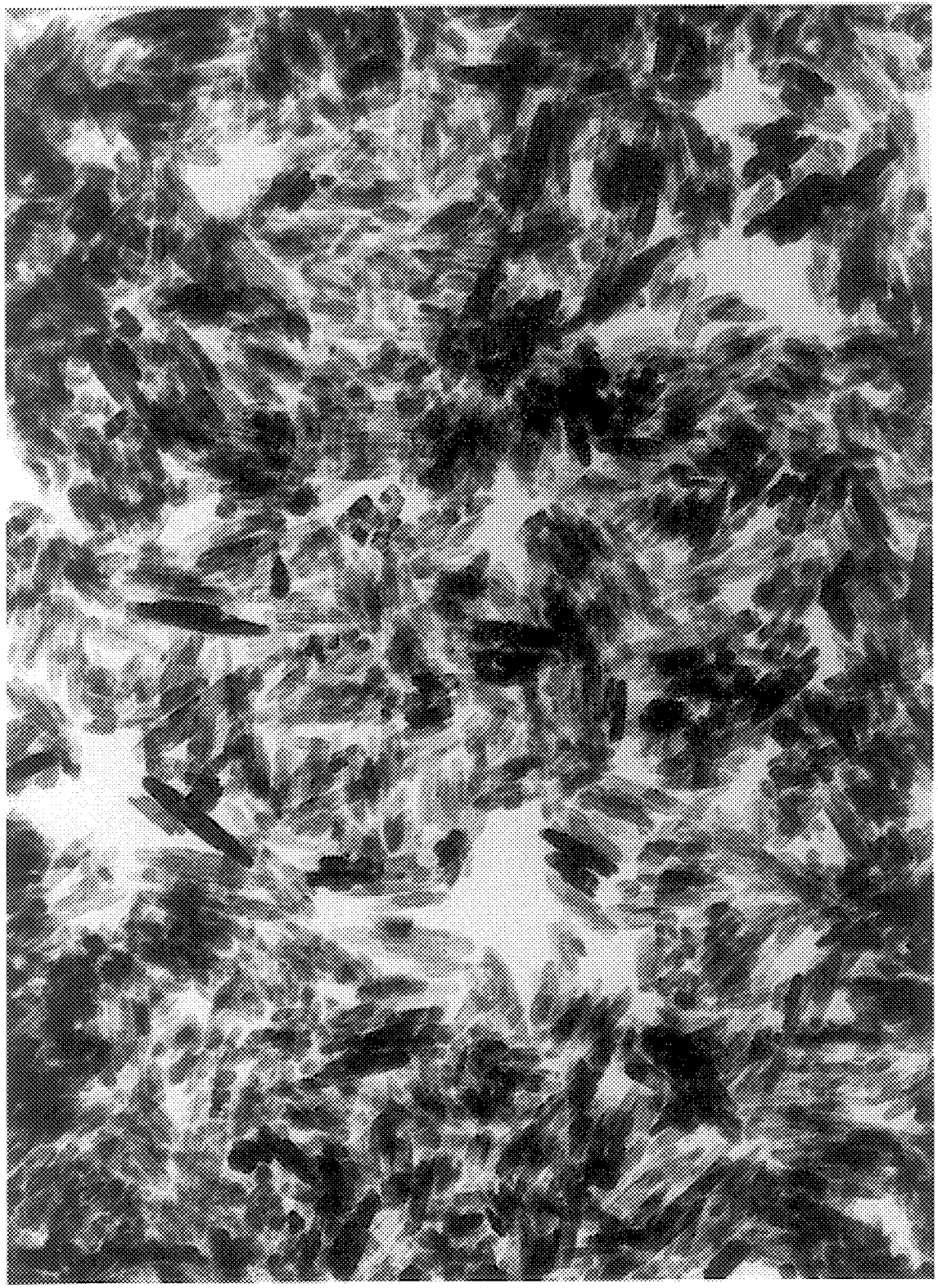
FIG. 12 is an electron micrograph (X150,000) in place of a drawing showing the particle structure of conventional needle shaped fine particles of titanium dioxide.

*[1]: (A) Rutile crystalline type, average particle size 0.03 μm. (Electron micrograph (×150,000) showing particle structure of spherical fine particles of titanium dioxide of (A) given in FIG. 11.)
*[2]: (B) Rutile crystalline type, average short diameter 0.008 μm, average long diameter 0.03 μm. (Electron micrograph (×150,000) showing particle structure of needle shaped fine particles of titanium dioxide of (B) given in FIG. 12.)
*[3]: (C) Rutile crystalline type, average short diameter 0.04 μm, average long diameter 0.1 μm. (Electron micrograph (×150,000) showing particle structure of spindle shaped fine particles of titanium dioxide of (C) given in FIG. 10.)

Example 2 and Comparative Example 3

Oily stick foundations comprising the formulations (parts by weight) listed in the following Table 2 were prepared by the method described below and measured for the UV protecting effect in the same way as Example 1. The results are shown in FIG. 3 and FIG. 4.

Figure 3:
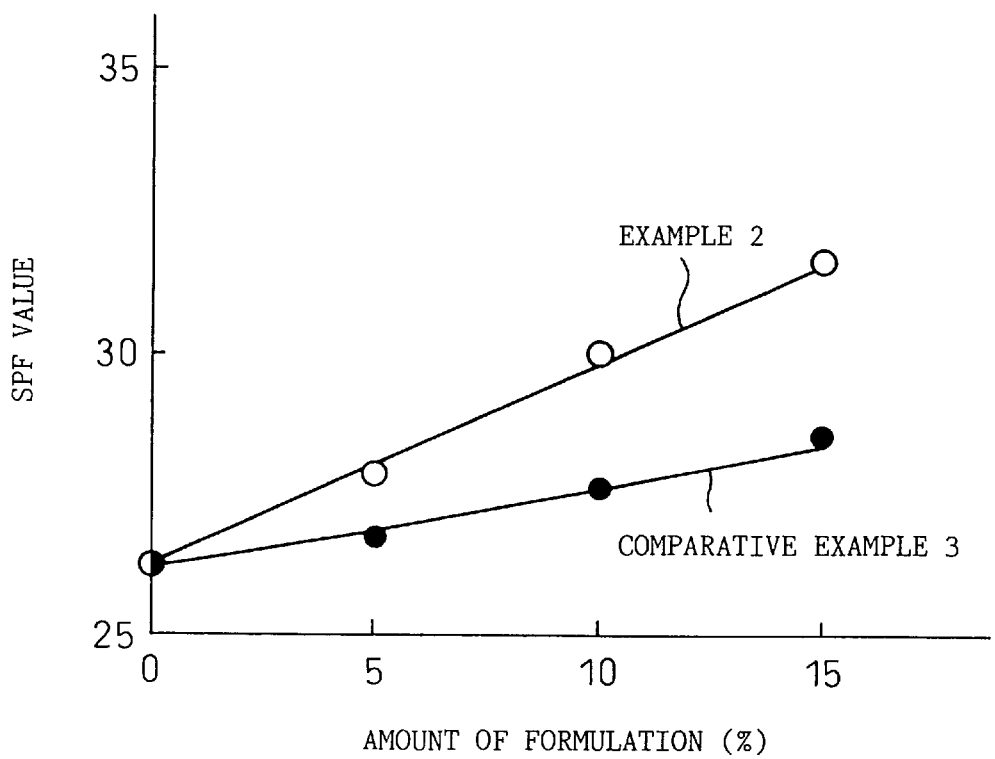
FIG. 3 is a graph showing the relationship between the amount of formulation and an SPF value of the spindle shaped fine particles of titanium dioxide of the present invention compared with the prior art.
Figure 4:
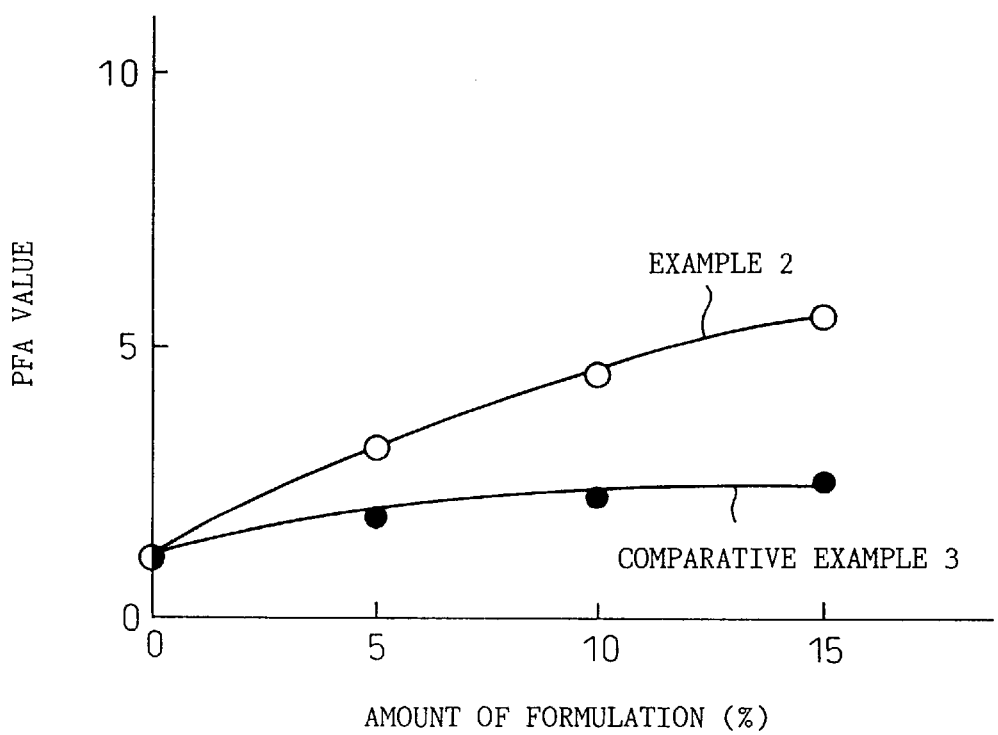
FIG. 4 is a graph showing the relationship between the amount of formulation and a PFA value of the spindle shaped fine particles of titanium dioxide of the present invention compared with the prior art.

As will be understood from FIG. 3 and FIG. 4, the cosmetic composition of the present invention contains as a pigment 0.2 μm or more of titanium dioxide and, compared with the cosmetic composition of Comparative Example 3 using fine particles of titanium dioxide of a small particle size which has been used as a conventional UV blocking agent, exhibits a higher UV protecting effect for both UVA and UVB. In particular, the effect is remarkable in the UVA region.

(Process of Production)

(1) to (5) were heated and melted at 85° C. To this mixture was added and mixed the sufficiently mixed and pulverized (6) to (14) while agitating. Then, the result and mixture was ground and pulverized by a colloid mill. The resultant mixture was deaerated, then was poured into a container at 70° C. and cooled.

TABLE 2

|  | Example 2 | Comparative Example 3 |
|---|---|---|
| (1) Carnauba wax | 1.5 | 1.5 |
| (2) Aristo wax | 4.0 | 4.0 |
| (3) Octylmethoxy cinnamate | 7.5 | 7.5 |
| (4) Squalane | 27.0 | 27.0 |
| (5) Liquid paraffin | 12.0 | 12.0 |
| (6) Kaolin | 5–15 | 5–15 |
| (7) Sericite | 9.0 | 9.0 |
| (8) Zinc oxide (0.2–0.5 μm) | 3.0 | 3.0 |
| (9) Bengara (0.2–0.5 μm) | 1.5 | 1.5 |
| (10) Yellow iron oxide (0.3–0.7 μm) | 4.0 | 4.0 |
| (11) Black iron oxide (0.2–0.5 μm) | 0.5 | 0.5 |
| (12) Nylon powder | 10.0 | 10.0 |
| (13) Aluminum stearate treated needle shaped fine particles of titanium dioxide (B) | — | 5–15 |
| (14) Aluminum stearate-treated spindle shaped fine particles of titanium dioxide (C) | 5–15 | — |

Examples 3 to 4 and Comparative Example 4

O/W emulsion type sunscreen creams comprising the formulations (parts by weight) listed in the following Table 3 were prepared by the method described later and measured for the UV protecting effect in the same way as Example 1. The results are shown in FIG. 5 and FIG. 6.

Figure 5:
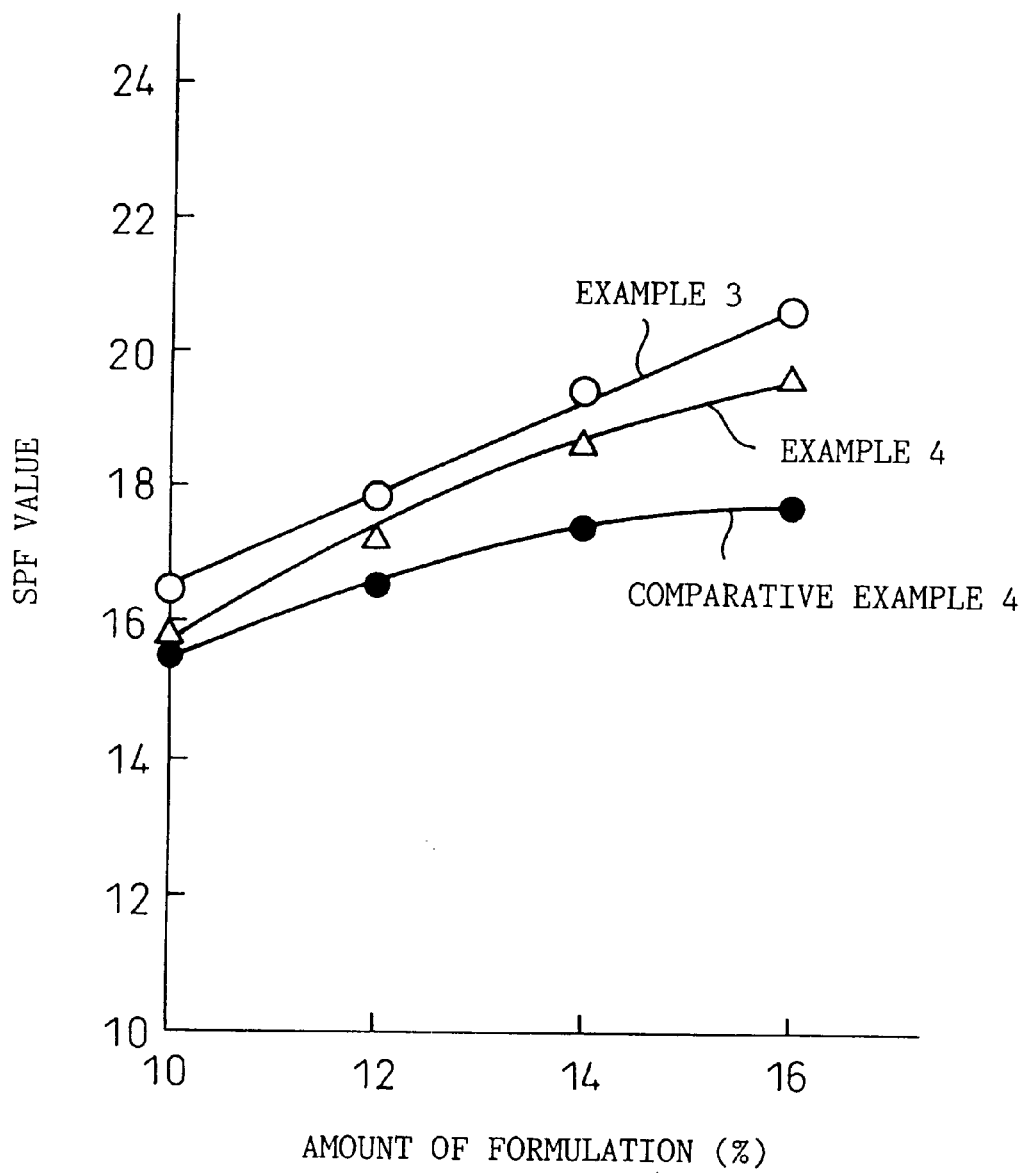
FIG. 5 is a graph showing the relationship between the amount of formulation and an SPF value of the spindle shaped fine particles of titanium dioxide of the present invention compared with the prior art.
Figure 6:
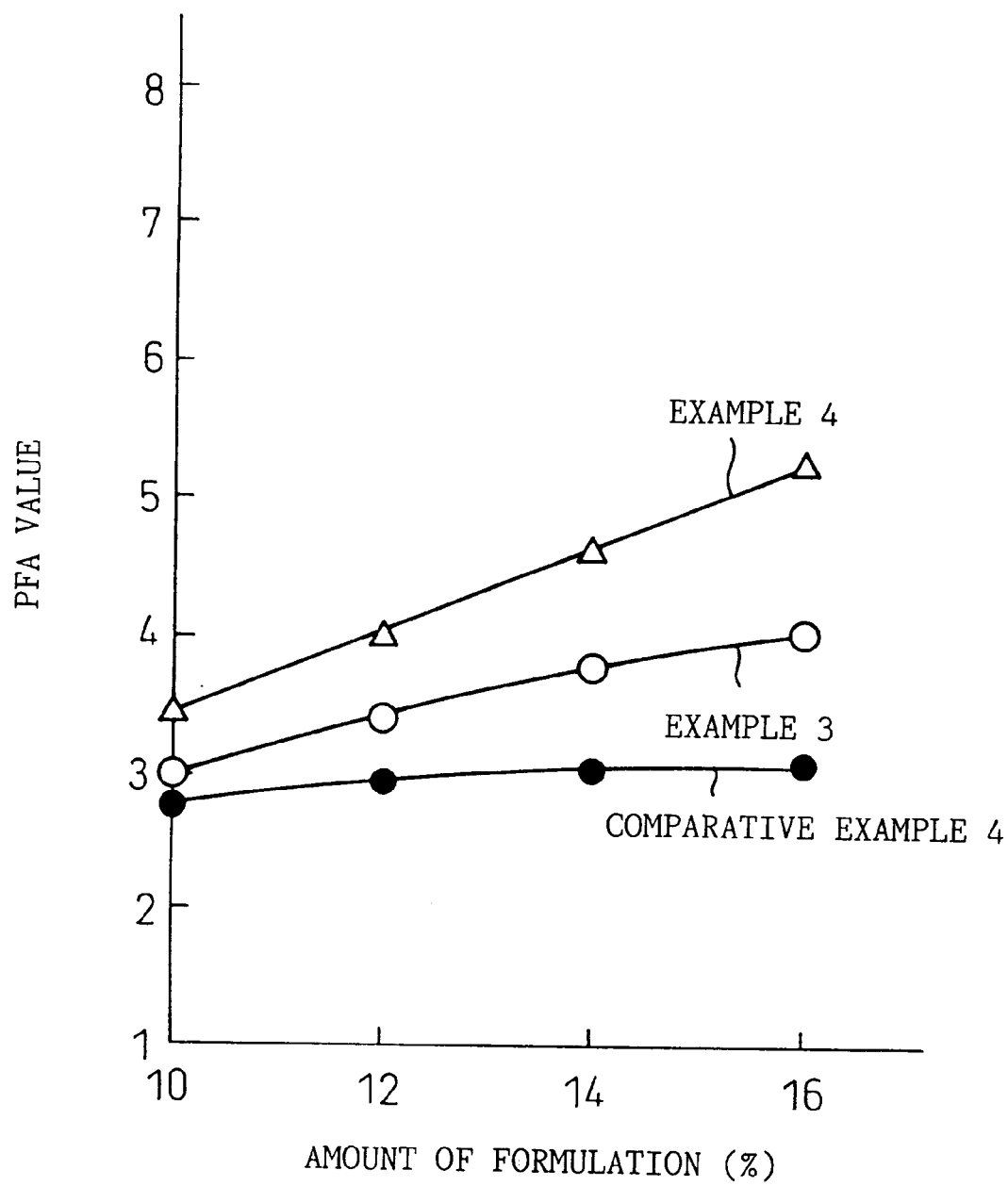
FIG. 6 is a graph showing the relationship between the amount of formulation and a PFA value of the spindle shaped fine particles of titanium dioxide of the present invention compared with the prior art.

As will be understood from FIG. 5 and FIG. 6, the cosmetics composition of the present invention, compared with the cosmetic composition of Comparative Example 4 using fine particles of titanium dioxide having a small particle size which has been used as a conventional UV blocking agent, exhibit a higher UV protecting effect for both UVA and UVB. In particular, the effect is remarkable in the UVA region.

(Process of Production)

The oil phase portion of (1) to (6) was heated and agitated at 70° C., (7) to (11) were completely melted at 70° C. to form an aqueous phase portion, then (12) was agitated and mixed with the powder portion of (13) or (14). Thereafter, the oil phase portion, was mixed with the aqueous phase portion, followed by emulsifing by a homogenizer. The emulsion was cooled by a heat exchanger to 30° C., then filled into a container.

TABLE 3

|  | Example | | Comparative |
|---|---|---|---|
|  | 3 | 4 | Example 4 |
| (1) Stearic acid | 2.0 | 2.0 | 2.0 |
| (2) Propylene glycol monostearate | 2.0 | 2.0 | 2.0 |
| (3) Cetanol | 2.5 | 2.5 | 2.5 |
| (4) Liquid lanolin | 2.0 | 2.0 | 2.0 |
| (5) Liquid paraffin | 5.0 | 5.0 | 5.0 |
| (6) Silicone oil | 5.0 | 5.0 | 5.0 |
| (7) Refined water | 58–64 | 58–64 | 58–64 |
| (8) Triethanol amine | 1.0 | 1.0 | 1.0 |
| (9) Bentonite | 0.8 | 0.8 | 0.8 |
| (10) Propylene glycol | 5.0 | 5.0 | 5.0 |
| (11) Methyl paraben | q.s. | q.s. | q.s. |
| (12) Alumina-treated needle shaped fine particles of titanium dioxide (D)*[4] | 4.0 | — | 4.0 |
| (13) Alumina-treated treated spherical fine particles of titanium dioxide (A) | — | — | 6–12 |
| (14) Alumina-treated spindle shaped fine particles of titanium dioxide (C) | 6–12 | 10–16 | — |

*[4]: (D) Rutile crystalline form, average short diameter 0.01 μm, average long diameter 0.07 μm.

Example 5 and Comparative Example 5

W/O emulsion type foundations comprising of the formulations (parts by weight) listed in the following Table 4 were prepared by the method described below and measured for the UV protecting effect in the same way as Example 1. The results are shown in FIG. 7 and FIG. 8.

Figure 7:
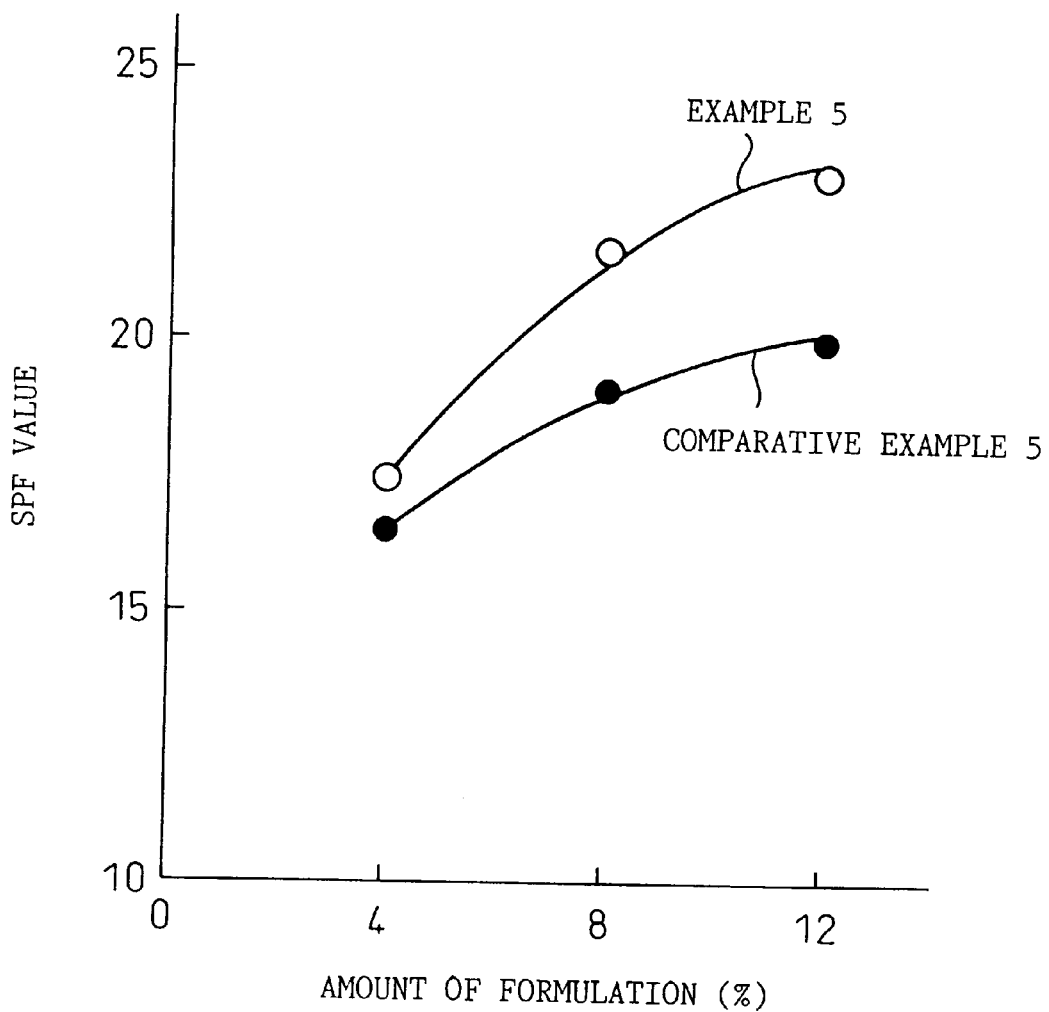
FIG. 7 is a graph showing the relationship between the amount of formulation and an SPF value of the spindle shaped fine particles of titanium dioxide of the present invention compared with the prior art.
Figure 8:
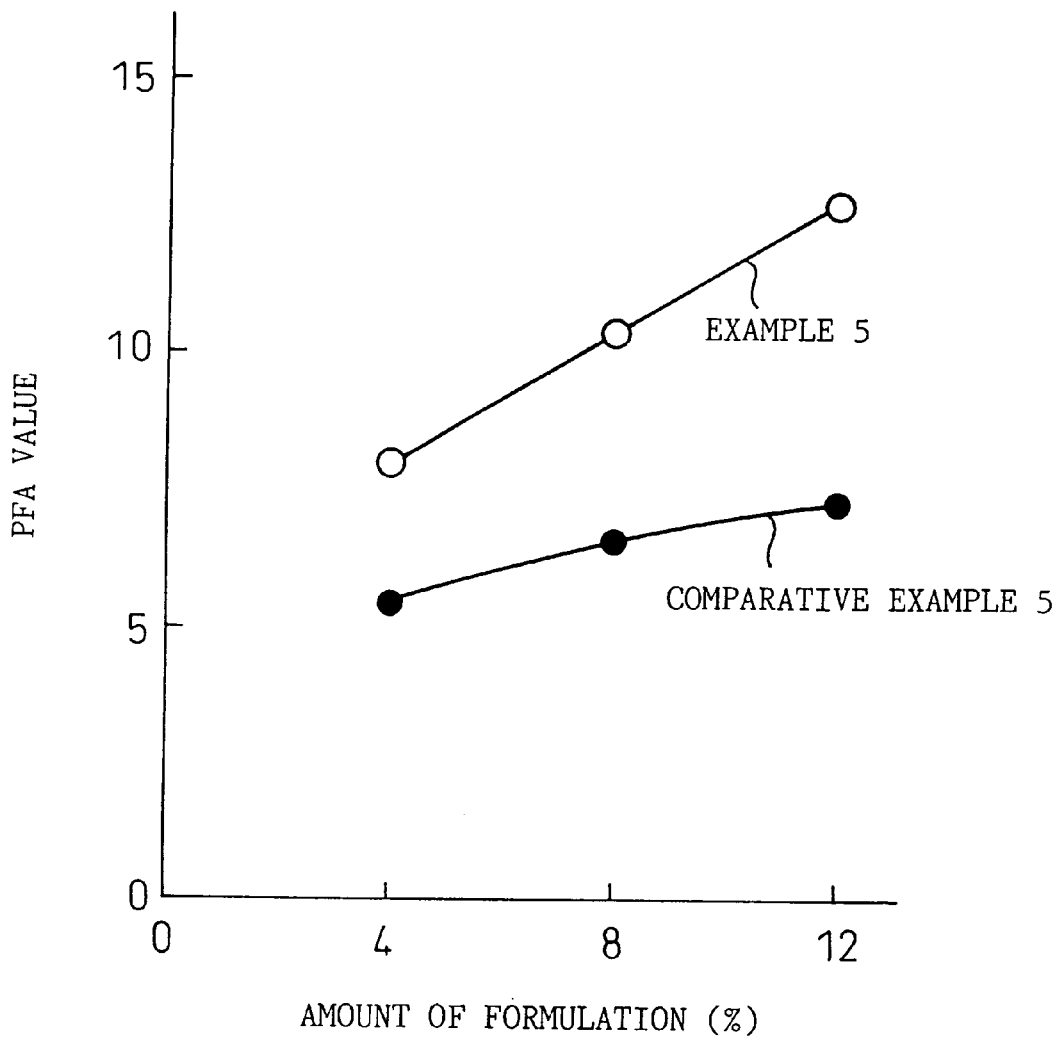
FIG. 8 is a graph showing the relationship between the amount of formulation and a PFA value of the spindle shaped fine particles of titanium dioxide of the present invention compared with the prior art.

As will be understood from FIG. 7 and FIG. 8, the cosmetic composition of the present invention, compared with the cosmetic composition of Comparative Example 5 containing as pigments metal oxides of 0.2 μm or more and using fine particles of titanium dioxide of a small particle size which has been used as a conventional UV blocking agent, exhibit a higher UV protecting effect for both UVA and UVB. In particular, the effect is remarkable in the UVA region.

(Process of Production)

The oil phase portion of (1) to (9) was heated and agitated at 70° C., then the powder portion of (10) to (16) was dispersed and mixed therein. The aqueous phase portion of

(17) and (18) was added and the mixture emulsified by a homogenizer, then was cooled to 30° C. by a heat exchanger and then filled in a container.

TABLE 4

|   | Example 5 | Comparative Example 5 |
|---|---|---|
| (1) Dimethyl polysiloxane | 7.0 | 7.0 |
| (2) Methylphenyl polysiloxane | 5.0 | 5.0 |
| (3) Decamethyl pentacyclosiloxane | 20.0 | 20.0 |
| (4) Squalane | 2.0 | 2.0 |
| (5) Trimethyl siloxy silicate | 3.0 | 3.0 |
| (6) Polyoxyethylene sorbitan fatty acid ester | 3.0 | 3.0 |
| (7) Polyether modified silicone | 4.0 | 4.0 |
| (8) Paraben | 0.1 | 0.1 |
| (9) Fragrance | q.s. | q.s. |
| (10) Dextrin fatty acid ester treated needle shaped fine particles of titanium dioxide (B) | — | 4.0–12.0 |
| (11) Dextrin fatty acid ester treated spindle shaped fine particles of titanium dioxide (C) | 4.0–12.0 | — |
| (12) Dextrin fatty acid ester treated sericite | 1.0–9.0 | 1.0–9.0 |
| (13) Dextrin fatty acid ester treated titanium dioxide (0.2–0.6 μm) | 8.0 | 8.0 |
| (14) Dextrin fatty acid ester treated cerium oxide (0.2–0.6 μm) | 2.0 | 2.0 |
| (15) Dextrin fatty acid ester treated kaolin | 2.0 | 2.0 |
| (16) Dextrin fatty acid ester treated iron oxide (0.2–0.5 μm) | 2.0 | 2.0 |
| (17) Butylene glycol | 5.0 | 5.0 |
| (18) Ion exchanged water | 23.9 | 23.9 |

Examples 6 to 7 and Comparative Examples 6 to 7

W/O (water in oil) emulsion type sunscreens comprising the formulations (parts by weight) listed in the following Table 6 were prepared by the method described below and evaluated as to feeling in use (roughness) by the following method. Further, they were measured for the UV protecting effect in the same way as Example 1. The results are shown together in Table 6.

As will be understood from Table 6, the spindle shaped fine particles of titanium dioxide according to the present invention, compared with the conventional needle shaped fine particles of titanium dioxide, exhibit a high PFA value showing the protective effect against UVA but exhibit a low SPF value showing the protective effect against UVB when metal oxide (titanium dioxide) for pigment use is not included having a size of more than 0.2 μm. However, when titanium dioxide for pigment use is included, the SPF value and PFA value both become higher in the case of spindle shaped fine particles of titanium dioxide than needle shaped fine particles of titanium dioxide. The needle shaped fine particles of titanium dioxide aggregate when titanium dioxide for pigment use is added causing a state like that of an ordered mixture and the inherent UVB protective effect is difficult to exhibit.

Further, in Comparative Example 7 in which titanium dioxide for pigment use and needle shaped fine particles of titanium dioxide are mixed together, a rough feeling is given and the usability is poor, while when spindle shaped fine particles of titanium dioxide are used, it was learned that an excellent feeling of use was maintained even when titanium dioxide for pigment use was added together.

(Method of Evaluation of Usability)

An expert panel of 20 women was used for an organoleptic evaluation of the roughness of the products of the Examples and the products of the comparative Examples when applied to the skin based on the criteria of Table 5.

TABLE 5

| Evaluation item | 1 | 2 | 3 | 4 | 5 |
|---|---|---|---|---|---|
| Roughness | None | Slightly | Normal | Some | Yes |

(Indication of results of evaluation)
++: 4.5 or more
+: 3.5 to less than 4.5
±: 2.5 to less than 3.5
−: 1.5 to less than 2.5
−−: Less than 1.5

(Process of Production)

(1) to (4) were mixed to make the oil phase portion. (5) was dispersed, then (6) to (8) were added and dispersed. (9) and (13) were melted at 50° C., then (10), (11), and (12) were added to make the aqueous phase portion. The aqueous phase portion was added to the oil phase portion and the two were emulsified by a homomixer. The emulsion was filled in a container.

TABLE 6

|   | Example | | Comparative Example | |
|---|---|---|---|---|
|   | 6 | 7 | 6 | 7 |
| (1) Dimethyl polysiloxane | 23.0 | 19.0 | 23.0 | 19.0 |
| (2) Decamethyl cyclopentasiloxane | 10.0 | 10.0 | 10.0 | 10.0 |
| (3) Organo modified dimethyl polysiloxane | 2.5 | 2.5 | 2.5 | 2.5 |
| (4) Diisostearate polyglyceryl | 0.5 | 0.5 | 0.5 | 0.5 |
| (5) Dimethyldistearyl ammonium hectorite | 1.5 | 1.5 | 1.5 | 1.5 |
| (6) Aluminum stearate treated needle shaped fine particles of titanium dioxide (B) | — | — | 7.0 | 7.0 |
| (7) Aluminum stearate treated spindle shaped fine particles of titanium dioxide (C) | 7.0 | 7.0 | — | — |
| (8) Aluminum stearate treated titanium dioxide (0.3–0.8 μm) | — | 6.0 | — | 6.0 |
| (9) Methyl paraben | 0.15 | 0.15 | 0.15 | 0.15 |
| (10) Ion exchange water | 44.3 | 42.3 | 44.3 | 42.3 |
| (11) Trysodium edetate | 0.05 | 0.05 | 0.05 | 0.05 |
| (12) Polyethylene glycol | 1.0 | 1.0 | 1.0 | 1.0 |
| (13) 1,3-butylene glycol | 10.0 | 10.0 | 10.0 | 10.0 |
| SPF value (in vivo: n = 10) | 16.4 | 22.7 | 18.1 | 19.2 |
| PFA value (in vivo: n = 10) | 4.61 | 10.0 | 2.39 | 8.14 |
| Roughness | ++ | + | ± | − |

Examples 8 to 11 and Comparative Examples 8 to 11

Solid foundations comprising the formulations (parts by weight) listed in the following Tables 7 and 8 were prepared by the method described later and measured for the UV protecting effect in the same way as Example 1. The results are shown in FIG. 9.

Figure 9:
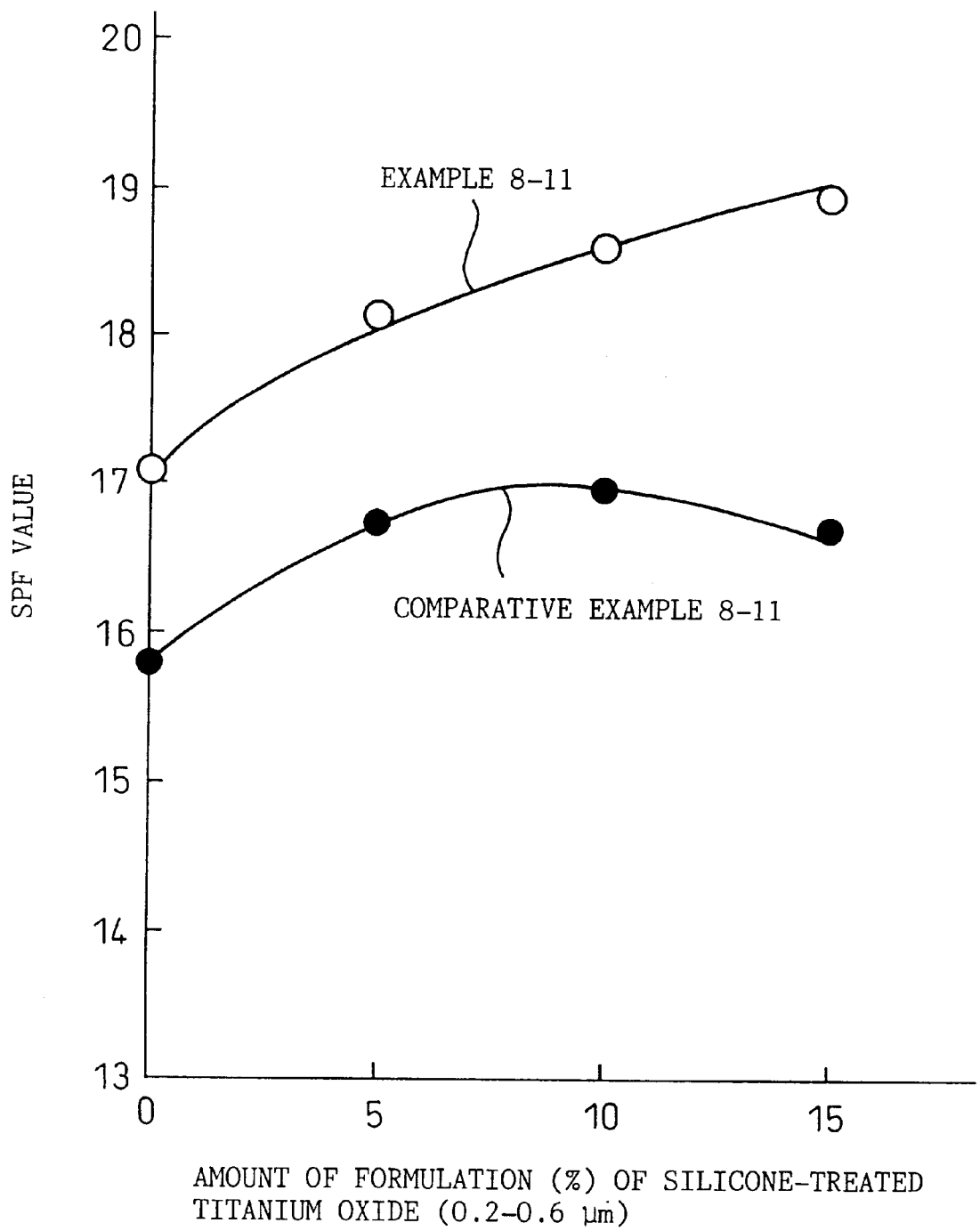
FIG. 9 is a graph showing the relationship between the amount of formulation and an SPF value of the spindle shaped fine particles of titanium dioxide of the present invention compared with the prior art.

As will be understood from FIG. 9, the spindle shaped fine particles of titanium dioxide according to the present invention protect against UVB, without being affected by the titanium dioxide for pigment use, and the SPF value rises along with the protection against UVA by the titanium dioxide for pigment use having the inherent UVA protective action. (It is known that UVA acts synergistically in the erythema reaction of UVB and exhibits a light reinforcing reaction. Accordingly, by protecting against UVA, the SPF value rises.)

However, spindle shaped fine particles of titanium dioxide are affected by the titanium dioxide for pigment use and aggregate, and therefore, the UVB protective effect increasingly drops along with the amount of titanium dioxide added. Accordingly, the SPF value gradually falls no matter how much the titanium dioxide for pigment use protects against UVA.

(Process of Production)

The powder portion of (1) to (11) was homogeneously mixed by a Henschel mixer, then the oil portion of (12) to (18) was added and the mixture was mixed for a certain time by a Henschel mixer. The resultant mixture was pulverized by a pulverizer, passed through a sieve, placed in a metal or plastic container, and compression molded to form the solid foundation.

TABLE 7

|  | Example | | | |
|---|---|---|---|---|
|  | 8 | 9 | 10 | 11 |
| (1) Sintered mica | 20.0 | 20.0 | 20.0 | 20.0 |
| (2) Silicone treated sericite | 21.35 | 16.35 | 11.35 | 6.35 |
| (3) Silicone treated phlogopite | 10.0 | 10.0 | 10.0 | 10.0 |
| (4) Talc | 10.0 | 10.0 | 10.0 | 10.0 |
| (5) Spherical PMMA resin powder | 10.0 | 10.0 | 10.0 | 10.0 |
| (6) Silicone treated bengara (0.2–0.5 μm) | 0.6 | 0.6 | 0.6 | 0.6 |
| (7) Silicone treated yellow iron oxide (0.3–0.7 μm) | 1.0 | 1.0 | 1.0 | 1.0 |
| (8) Silicone treated black iron oxide (0.2–0.5 μm) | 0.05 | 0.05 | 0.05 | 0.05 |
| (9) Silicone treated titanium dioxide (0.2–0.6 μm) | — | 5.0 | 10.0 | 15.0 |
| (10) Silicone treated spindle shaped fine particles of titanium dioxide (C) | 10.0 | 10.0 | 10.0 | 10.0 |
| (11) Silicone treated needle shaped fine particles of titanium dioxide (D) | — | — | — | — |
| (12) Dimethyl polysiloxane | 3.0 | 3.0 | 3.0 | 3.0 |
| (13) Methylphenyl polysiloxane | 3.5 | 3.5 | 3.5 | 3.5 |
| (14) Liquid paraffin | 2.0 | 2.0 | 2.0 | 2.0 |
| (15) Vaseline | 3.0 | 3.0 | 3.0 | 3.0 |
| (16) Sorbitan sesquiisostearate | 1.5 | 1.5 | 1.5 | 1.5 |
| (17) Antioxidant | q.s. | q.s. | q.s. | q.s. |
| (18) Fragrance | q.s. | q.s. | q.s. | q.s. |

TABLE 8

|  | Comparative Example | | | |
|---|---|---|---|---|
|  | 8 | 9 | 10 | 11 |
| (1) Sintered mica | 20.0 | 20.0 | 20.0 | 20.0 |
| (2) Silicone treated sericite | 21.35 | 16.35 | 11.35 | 6.35 |

TABLE 8-continued

|  | Comparative Example | | | |
|---|---|---|---|---|
|  | 8 | 9 | 10 | 11 |
| (3) Silicone treated phlogopite | 10.0 | 10.0 | 10.0 | 10.0 |
| (4) Talc | 10.0 | 10.0 | 10.0 | 10.0 |
| (5) Spherical PMMA resin powder | 10.0 | 10.0 | 10.0 | 10.0 |
| (6) Silicone treated bengara (0.2–0.5 μm) | 0.6 | 0.6 | 0.6 | 0.6 |
| (7) Silicone treated yellow iron oxide (0.3–0.7 μm) | 1.0 | 1.0 | 1.0 | 1.0 |
| (8) Silicone treated black iron oxide (0.2–0.5 μm) | 0.05 | 0.05 | 0.05 | 0.05 |
| (9) Silicone treated titanium dioxide (0.2–0.6 μm) | — | 5.0 | 10.0 | 15.0 |
| (10) Silicone treated spindle shaped fine particles of titanium dioxide (C) | — | — | — | — |
| (11) Silicone treated needle shaped fine particles of titanium dioxide (D) | 10.0 | 10.0 | 10.0 | 10.0 |
| (12) Dimethyl polysiloxane | 3.0 | 3.0 | 3.0 | 3.0 |
| (13) Methylphenyl polysiloxane | 3.5 | 3.5 | 3.5 | 3.5 |
| (14) Liquid paraffin | 2.0 | 2.0 | 2.0 | 2.0 |
| (15) Vaseline | 3.0 | 3.0 | 3.0 | 3.0 |
| (16) Sorbitan sesquiisostearate | 1.5 | 1.5 | 1.5 | 1.5 |
| (17) Antioxidant | q.s. | q.s. | q.s. | q.s. |
| (18) Fragrance | q.s. | q.s. | q.s. | q.s. |

Examples 12 to 13 and Comparative Examples 12 to 13

W/O (water in oil) emulsion type cream sunscreens comprising the formulations (parts by weight) listed in the following Table 9 were prepared by the method described below and measured for the UV protecting effect in the same way as Example 1. The results are shown together in Table 9.

(Process of Production)

The aqueous phase portion of (1), (2), and (11) and the oil phase portion of (3) to (8) and (12) were heated to 70° C. and allowed to melt. In the oil phase portion was well dispersed either one of the fine particles of titanium dioxide (9) and (10). The aqueous phase portion was then added, while agitating by a homogenizer to form the emulsion. This was cooled to room temperature, then filled in a container.

As will be understood from Table 9, the spindle shaped fine particles of titanium dioxide according to the present invention, compared with the conventional needle shaped fine particles of titanium dioxide, exhibit a high PFA value showing the protective effect against UVA but exhibit a low SPF value showing the protective effect against UVB when silicone resin is not added. However, when silicone resin is added, the SPF value and PFA value both become higher in the case of spindle shaped fine particles of titanium dioxide than needle shaped fine particles of titanium dioxide. The needle shaped fine particles of titanium dioxide aggregate when silicone resin is added and the inherent UVB protective effect is difficult to exhibit.

TABLE 9

| | Example | | Comparative Example | |
|---|---|---|---|---|
| | 12 | 13 | 12 | 13 |
| (1) Ion exchange water | 38.5 | 38.5 | 38.5 | 38.5 |
| (2) 1,3-butylene glycol | 5.0 | 5.0 | 5.0 | 5.0 |
| (3) Decamethyl cyclopentasiloxane | 23.0 | 19.0 | 23.0 | 19.0 |
| (4) Dimethylpolysiloxane (6 cs) | 8.0 | 8.0 | 8.0 | 8.0 |
| (5) Trimethyl siloxysilicate (silicone resin) | — | 4.0 | — | 4.0 |
| (6) Squalane | 10.0 | 10.0 | 10.0 | 10.0 |
| (7) Glycerine diisostearate | 3.0 | 3.0 | 3.0 | 3.0 |
| (8) Organic modified montmorillonite | 1.5 | 1.5 | 1.5 | 1.5 |
| (9) Aluminum stearate treated needle shaped fine particles of titanium dioxide (B) | — | — | 10.0 | 10.0 |
| (10) Aluminum stearate treated spindle shaped fine particles of titanium dioxide (C) | 10.0 | 10.0 | — | — |
| (11) Paraben | q.s. | q.s. | q.s. | q.s. |
| (12) Fragrance | q.s. | q.s. | q.s. | q.s. |
| SPF value (in vitro: n = 10) | 22.4 | 24.2 | 23.8 | 21.0 |
| PFA value (in vitro: n = 10) | 3.6 | 4.1 | 2.7 | 2.1 |

Industrial Applicability

As explained above, the cosmetic composition comprising the spindle shaped fine particles of titanium dioxide according to the present invention has a protective effect in a broad UV region of UVB and UVA and can simultaneously prevent erythema and melanism caused due to UV rays. Further, the fine particles of titanium dioxide according to the present invention do not aggregate even if formulated together with titanium dioxide or metal iron oxide used for pigments, so there is no rough feeling in a cosmetic containing the same and a product with a smooth feel is obtained.

What is claimed is:

1. A cosmetic composition comprising spindle shaped fine particles of titanium dioxide having an average short diameter of 0.03 to 0.06 μm, an average long diameter of 0.08 to 0.12 μm, and an aspect ratio of long diameter/short diameter of 2 to 4, formulated therein.

2. The cosmetic composition as claimed in claim 1, wherein the average short diameter is 0.03 to 0.04 μm, the average long diameter is 0.09 to 0.10 μm, and the aspect ratio is 2.5 to 3.5.

3. The cosmetic composition as claimed in claim 1, wherein a metal having an average particle size of not less than 0.2 μm is further formulated therein.

4. The cosmetic composition as claimed in claim 3, wherein the metal oxide is titanium dioxide, zinc oxide, iron oxide, or cerium oxide.

5. The cosmetic composition as claimed in claim 3, wherein the average short diameter of the spindle shaped particles of titanium dioxide is 0.03 to 0.04 μm, the average long diameter is 0.09 to 0.10 μm, and the aspect ratio is 2.5 to 3.5.

6. The cosmetic composition as claimed in claim 1, wherein a silicone resin is further formulated therein.

7. The cosmetic composition as claimed in claim 1, wherein the spindle shaped particles of titanium dioxide range from 0.5 to 70% by weight.

8. The cosmetic composition as claimed in claim 1, wherein the spindle shaped particles of titanium dioxide range from 2.0 to 40% by weight.

9. The cosmetic composition as claimed in claim 1, wherein from 0.5–50% by weight needle shaped fine particles of titanium dioxide having an average short diameter of 0.005 to 0.02 μm and an average long diameter of 0.01 to 0.1 μm are further formulated therein.

10. The cosmetic composition as claimed in claim 1, wherein an inorganic powder, an organic powder, an inorganic pigment, an organic pigment or a mixture thereof is further formulated therein.

11. The cosmetic composition as claimed in claim 1, wherein the titanium dioxide in the composition is in the form of spindle shaped fine particles.

* * * * *